United States Patent
Showalter et al.

(10) Patent No.: US 6,313,292 B1
(45) Date of Patent: Nov. 6, 2001

(54) PROCESS FOR PREPARING 4,6-DISUBSTITUTED PYRIDO[3,4-D]PYRIMIDINES

(75) Inventors: H. D. H. Showalter; Roy T. Winters, both of Ann Arbor, MI (US); Gordon W. Rewcastle, Manurewa; William A. Denny, Pakuranga, both of (NZ)

(73) Assignee: Warner-Lambert Company, Morris Plains, MI (US)

( * ) Notice: Subject to any disclaimer, the term of this patent is extended or adjusted under 35 U.S.C. 154(b) by 0 days.

(21) Appl. No.: 09/101,105

(22) PCT Filed: Jan. 7, 1997

(86) PCT No.: PCT/US97/00127

§ 371 Date: Jul. 1, 1998

§ 102(e) Date: Jul. 1, 1998

(87) PCT Pub. No.: WO97/26259

PCT Pub. Date: Jul. 24, 1997

Related U.S. Application Data

(60) Provisional application No. 60/010,066, filed on Jan. 16, 1996.

(51) Int. Cl.$^7$ ............................................. C07D 471/04
(52) U.S. Cl. ............................................. 544/277
(58) Field of Search ............................................. 544/277

(56) References Cited

U.S. PATENT DOCUMENTS

| | | | | |
|---|---|---|---|---|
| 3,670,007 | * | 6/1972 | Ferris | 260/465.5 |
| 3,965,109 | * | 6/1976 | Tomlin et al. | 546/295 |
| 4,547,506 | * | 10/1985 | Ife | 544/320 |
| 4,789,624 | * | 12/1988 | Sakanoue et al. | 430/372 |
| 5,001,137 | * | 3/1991 | Oe et al. | 514/342 |
| 5,136,031 | * | 8/1992 | Khan et al. | 536/122 |
| 5,230,827 | * | 7/1993 | Reiffenrath et al. | 252/299.61 |
| 5,260,307 | * | 11/1993 | Ackermann et al. | 514/323 |
| 5,358,948 | * | 10/1994 | Bradshaw et al. | 514/252 |
| 5,364,862 | * | 11/1994 | Spada et al. | 514/303 |
| 5,457,105 | * | 10/1995 | Barker | 544/284 |
| 5,464,855 | * | 11/1995 | Capiris et al. | 514/382 |
| 5,620,959 | * | 4/1997 | Leban et al. | 514/16 |
| 5,654,307 | * | 8/1997 | Bridges et al. | 514/258 |
| 5,714,490 | * | 2/1998 | Saksena et al. | 514/252 |
| 5,763,604 | * | 6/1998 | Ackermann et al. | 544/160 |
| 5,773,411 | * | 6/1998 | Wells et al. | 514/11 |
| 5,824,657 | * | 10/1998 | Hill et al. | 514/46 |
| 5,852,035 | * | 12/1998 | Pamukcu et al. | 514/293 |
| 5,859,257 | * | 1/1999 | Talley | 548/247 |
| 5,869,484 | * | 2/1999 | Terni et al. | 514/231.2 |
| 5,891,894 | * | 4/1999 | Bernat et al. | 514/340 |
| 5,914,319 | * | 6/1999 | Schacht et al. | 514/19 |
| 5,916,899 | * | 6/1999 | Kiely et al. | 514/309 |
| 5,917,034 | * | 6/1999 | Brown et al. | 540/597 |

FOREIGN PATENT DOCUMENTS

95/19774 * 7/1995 (WO) .

OTHER PUBLICATIONS

Rewcastle et al., "Tyrosine Kinase Inhibitors 10.," *J. Med. Chem.*, vol. 39, No. 9, pp. 1823–1834, Apr. 1996.*

Berge, S. M. et al., "Pharmaceutical Salts," *Journal of Pharmaceutical Sciences*, vol. 66, No. 1, pp. 1–19 (Jan. 1977).

Clark, J. H. et al., "The Synthesis of Organofluorine Compounds Using Potassium Fluoride–Tetraphenylphosphonium Bromide Systems," *Tetrahedron Letters*, vol. 28, No. 1, pp. 111–114 (1987).

Finger, G. C. et al., "Aromatic Fluorine Compounds. IX. 2–Fluoropyridines," *The Journal of the American Chemical Society*, vol. 81, pp. 2674–2675 (Jun. 5, 1959).

Finger, G. C. et al., "Aromatic Fluorine Compounds. X. The 2,3– and 2,6–Difluoropyridines," *The Journal of Organic Chemistry*, vol. 27, pp. 3965–3968 (Nov. 1962).

Fry, D. W. et al., "Biochemical and Antiproliferative Properties of 4–[Ar(alk)ylamino]pyridopyrimidines, a New Chamical Class of Potent and Specific Epidermal Growth Factor Receptor Tyrosine Kinase Inhibitor," *Biochemical Pharmacology*, vol. 54, No. 8, pp. 877–887 (Oct. 15, 1997).

Rewcastle, G. W. et al., "Synthesis of 6–substituted pyrido[3,4–d]pyrimidin–4(3H)–ones via directed lithiation of 2–substituted 5–aminopyridine derivatives," *Journal of the Chemical Society, Perkin Trans. 1*, pp. 2221–2226 (1996).

Rewcastle, G. W. et al., "Tyrosine Kinase Inhibitors. 14. Structure–Activity Relationships for Methylamino–Substituted Derivatives of 4–[(3–Bromophenyl)amino]–6–(methylamino)–pyrido[3,4–d]pyrimidine (PD 158780), a Potent and Specific Inhibitor of the Tyrosine Kinase Activity of Receptors for the EGF Family of Growth Factors," *Journal of Medicinal Chemistry*, vol. 41, No. 5, pp. 742–751 (1998).

Smaill, J. B. et al., "Tyrosine Kinase Inhibitors. 15. 4–(Phenylamino) quinazoline and 4–(Phenylamino)pyridol[d]pyrimidine Acrylamides as Irreversible Inhibitors of the ATP Binding Site of the Epidermal Growth Factor Receptor," *J. Med. Chem*, vol. 42, pp. 1803–1815 (1999).

* cited by examiner

*Primary Examiner*—Richard L. Raymond
*Assistant Examiner*—Venkataraman Balasubramanian
(74) *Attorney, Agent, or Firm*—Merchant & Gould P.C.

(57) ABSTRACT

An improved process for the preparation of 4,6-disubstituted pyrido[3,4-d]pyrimidines is described where 5-amino-2-fluoropyridine is converted in seven operations to the desired products, as well as other valuable intermediates used in the process.

20 Claims, No Drawings

PROCESS FOR PREPARING 4,6-DISUBSTITUTED PYRIDO[3,4-D]PYRIMIDINES

This application is based upon PCT application Ser. No. PCT/US97/00127, filed Jan. 7, 1997, which claims priority from U.S. Provisional Application Ser. No. 60/010,066, filed Jan. 16, 1996.

BACKGROUND OF THE INVENTION

U.S. Pat. No. 5,654,307 which is herein incorporated by reference discloses bicyclic compounds which includes a series of 4,6-disubstituted pyrido[3,4-d]pyrimidines.

The compounds disclosed in the above United States Patent are useful in inhibiting the epidermal growth factor receptor and related receptors and, in particular, their tyrosine kinase activity, and thus are useful in the treatment of proliferative diseases including cancer, psoriasis, proliferative glomerulonephritis and diabetes-induced renal disease, pancreatitis, and as contraceptives. The aforementioned compounds have been prepared by a synthetic route which affords the target compounds in extremely low yields, i.e., in less than 0.34% overall yield from the starting material, 2-chloro-5-nitropyridine, requires chromatographic purification at several stages and furthermore, is difficult to conduct on a large scale.

The object of the present invention is an improved process for preparing the compounds described above on a large scale using inexpensive starting materials.

SUMMARY OF THE INVENTION

Accordingly, a first aspect of the present invention is a novel process for the preparation of a compound of Formula I

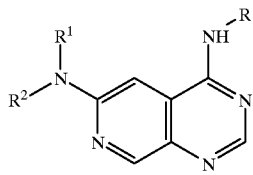

wherein R is aryl, alkyl, or arylalkyl;

$R^1$ and $R^2$ are the same or different and each is selected from the group consisting of:
 hydrogen,
 alkyl,
 hydroxyalkyl,
 dihydroxyalkyl,
 aminoalkyl,
 diaminoalkyl,
 carboxyalkyl,
 hydroxyalkylaminoalkyl,
 dihydroxyalkylaminoalkyl, and
 $R^1$ and $R^2$ may be combined with N to form a 5- or 6-membered ring optionally containing an N, O, or S atom wherein the N atom may be optionally substituted by an alkyl group; and pharmaceutically acceptable salts thereof which comprises:

Step (A) reaction of the compound of Formula X

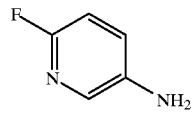

with a tertiary butoxycarbonyl (Boc) reagent in the presence of a solvent to afford the compound of Formula IX

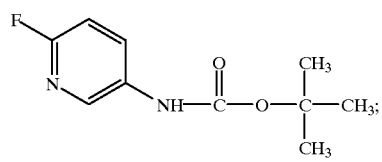

Step (B) reaction of the compound of Formula IX with a base and a carboxylate source in the presence of a solvent to afford the compound of Formula VIII

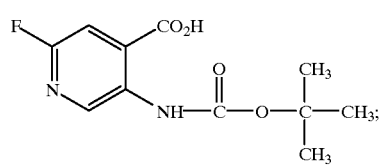

Step (C) reaction of the compound of Formula VIII with a Boc cleaving reagent in a solvent to afford the compound of Formula VII

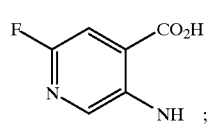

Step (D) reaction of the compound of Formula VII with a annulating reagent in a solvent to afford the compound of Formula VI

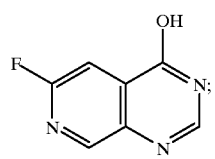

Step (E) reaction of the compound of Formula VI with a chlorinating reagent in a solvent to afford the compound of Formula V

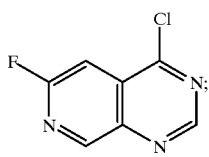

Step (F) reaction of the compound of Formula V with a compound of Formula IV

R—NH$_2$  IV wherein R is as defined above in a solvent to afford a compound of Formula II

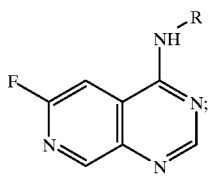

Step (G) reaction of a compound of Formula II with a compound of Formula III

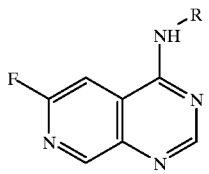

wherein R$^1$ and R$^2$ are as defined above in a solvent to afford a compound of Formula I; and Step (H), if desired, converting a compound of Formula I to a corresponding pharmaceutically acceptable salt by conventional means, and if so desired, converting the corresponding pharmaceutically acceptable salt to a compound of Formula I by conventional means.

A second aspect of the present invention is an improved process for the preparation of a compound of Formula II

II (structure)

wherein R is aryl, alkyl, or arylalkyl; and pharmaceutically acceptable salts thereof which comprises:
Step (A) reaction of the compound of Formula X

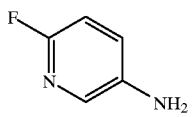

with a Boc reagent in the presence of a solvent to afford the compound of Formula IX

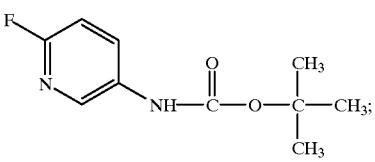

Step (B) reaction of the compound of Formula IX with a base and a carboxylate source in the presence of a solvent to afford the compound of Formula VIII

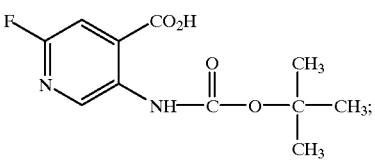

Step (C) reaction of the compound of Formula VIII with a Boc cleaving reagent in a solvent to afford the compound of Formula VII

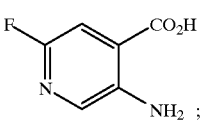

Step (D) reaction of the compound of Formula VII with a annulating reagent in a solvent to afford the compound of Formula VI

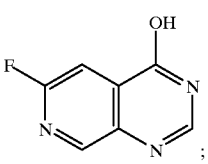

Step (E) reaction of the compound of Formula VI with a chlorinating reagent in a solvent to afford the compound of Formula V

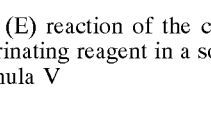

Step (F) reaction of the compound of Formula V with a compound of Formula IV

R—NH$_2$  IV wherein R is as defined above in a solvent to afford a compound of Formula II; and
Step (G), if desired, converting a compound of Formula II to a corresponding pharmaceutically acceptable salt by conventional means, and if so desired, converting the corresponding pharmaceutically acceptable salt to a compound of Formula II by conventional means.

A third aspect of the present invention is a novel process for the preparation of the compound of

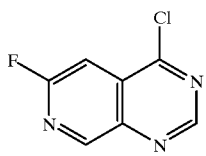

V and pharmaceutically acceptable salts thereof which comprises:

Step (A) reaction of the compound of Formula X

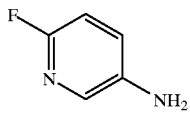

X with a Boc reagent in the presence of a solvent to afford the compound of Formula IX

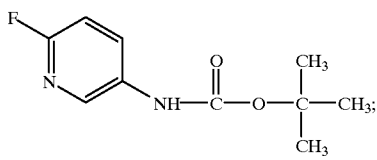

IX

Step (B) reaction of the compound of Formula IX with a base and a carboxylate source in the presence of a solvent to afford the compound of Formula VIII

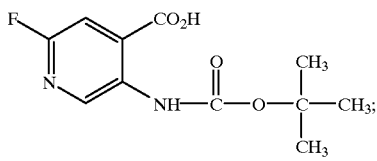

VIII

Step (C) reaction of the compound of Formula VIII with a Boc leaving reagent in a solvent to afford the compound of Formula VII

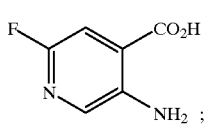

VII

Step (D) reaction of the compound of Formula VII with a annulating reagent in a solvent to afford the compound of Formula VI

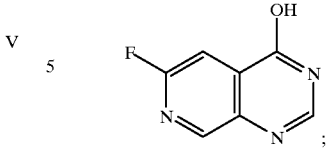

VI

Step (E) reaction of the compound of Formula VI with a chlorinating reagent in a solvent to afford the compound of Formula V; and Step (F), if desired, converting the compound of Formula V to a corresponding pharmaceutically acceptable salt by conventional means, and if so desired, converting the corresponding pharmaceutically acceptable salt to the compound of Formula V by conventional means.

A fourth aspect of the present invention is a novel process for the preparation of the compound of

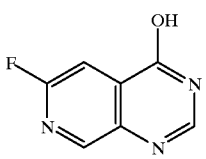

VI and pharmaceutically acceptable salts thereof which comprises:

Step (A) reaction of the compound of Formula X

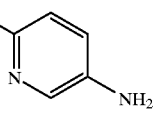

X with a Boc reagent in the presence of a solvent to afford the compound of Formula IX

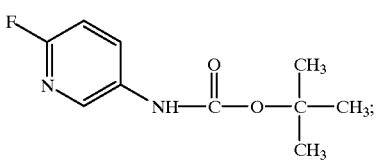

IX

Step (B) reaction of the compound of Formula IX with a base and a carboxylate source in the presence of a solvent to afford the compound of Formula VIII

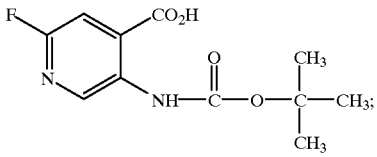

VIII

Step (C) reaction of the compound of Formula VIII with a Boc cleaving reagent in a solvent to afford the compound of Formula VII

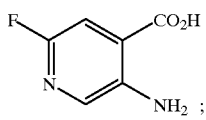

Step (D) reaction of the compound of Formula VII with a annulating reagent in a solvent to afford the compound of Formula VI; and Step (E), if desired, converting the compound of Formula VI to a corresponding pharmaceutically acceptable salt by conventional means, and if so desired, converting the corresponding pharmaceutically acceptable salt to the compound of Formula VI by conventional means.

A fifth aspect of the present invention is a novel process for the preparation of the compound of

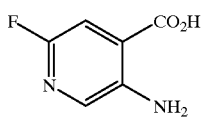

and pharmaceutically acceptable salts thereof which comprises: Step (A) reaction of the compound of Formula X

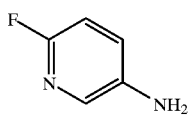

with a Boc reagent in the presence of a solvent to afford the compound of Formula IX

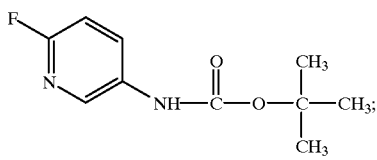

Step (B) reaction of the compound of Formula IX with a base and a carboxylate source in the presence of a solvent to afford the compound of Formula VIII

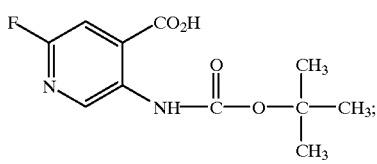

Step (C) reaction of the compound of Formula VIII with a Boc cleaving reagent in a solvent to afford the compound of Formula VII; and Step (D), if desired, converting the compound of Formula VII to a corresponding pharmaceutically acceptable salt by conventional means, and if so desired, converting the corresponding pharmaceutically acceptable salt to the compound of Formula VII by conventional means.

A sixth aspect of the present invention is a novel process for the preparation of the compound of

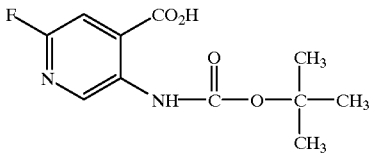

and pharmaceutically acceptable salts thereof which comprises: Step (A) reaction of the compound of Formula X

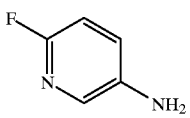

with a Boc reagent in the presence of a solvent to afford the compound of Formula IX

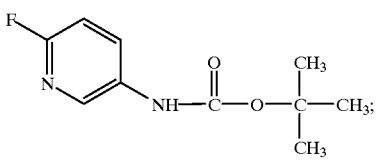

Step (B) reaction of the compound of Formula IX with a base and a carboxylate source in the presence of a solvent to afford the compound of Formula VIII; and Step (C), if desired, converting the compound of Formula VIII to a corresponding pharmaceutically acceptable salt by conventional means, and if so desired, converting the corresponding pharmaceutically acceptable salt to the compound of Formula VIII by conventional means.

A seventh aspect of the present invention is a novel process for the preparation of the compound of

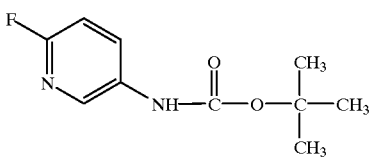

and pharmaceutically acceptable salts thereof which comprises: Step (A) reaction of the compound of Formula X

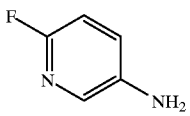

with a Boc reagent in the presence of a solvent to afford the compound of Formula IX; and step (B), if desired, converting the compound of Formula IX to a corresponding pharmaceutically acceptable salt by conventional means, and if so desired, converting the corresponding pharmaceutically acceptable salt to the compound of Formula IX by conventional means.

An eighth aspect of the present invention is a novel intermediate of Formula II

II

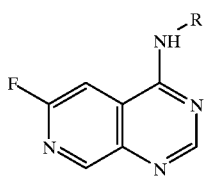

wherein R is aryl, alkyl, or arylalkyl; and
a pharmaceutically acceptable salt thereof; with the exclusion of 4[(3-bromophenyl)amino]-6-fluoropyrido[3,4-d]pyrimidine.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group, a naphthyl group, a phenyl group substituted by 1 to 4 substituents selected from alkyl as defined above, alkoxy as defined below, thioalkoxy as defined below, hydroxy, halogen, trifluoromethyl, amino, alkylamino as defined above for alkyl, dialkylamino as defined for alkyl, N-acetylamino, cyano or nitro, or a naphthyl group substituted by 1 to 4 substituents as defined above for a phenyl group substituted by 1 to 4 substituents.

The terms "alkoxy" and "thioalkoxy" are O-alkyl or S-alkyl as defined above for alkyl.

The term "arylalkyl" means an aromatic radical attached to an alkyl radical wherein aryl and alkyl are as defined above, for example, benzyl, naphthylmethyl, and the like.

The term "hydroxyalkyl" means a hydroxy group attached to an alkyl radical wherein alkyl is as defined above.

The term "dihydroxyalkyl" means two hydroxy groups attached to an alkyl radical wherein alkyl is as defined above.

The term "aminoalkyl" means an amino group attached to an alkyl radical wherein alkyl is as defined above.

The term "diaminoalkyl" means two amino groups attached to an alkyl radical wherein alkyl is as defined above.

The term "carboxyalkyl" means a carboxy group attached to an alkyl radical wherein alkyl is as defined above.

The term "hydroxyalkylaminoalkyl" means a "hydroxyalkyl" group attached to an aminoalkyl radical wherein hydroxyalkyl and aminoalkyl are as defined above.

The term "dihydroxyalkylaminoalkyl" means a dihydroxyalkyl group attached to an aminoalkyl radical wherein dihydroxyalkyl and aminoalkyl are as defined above.

The term "halogen" or "halo" means iodine, bromine, chlorine, and fluorine.

The term "noble metal" means platinum, palladium, rhodium, ruthenium, and the like.

The compounds of Formula I are capable of further forming pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 66:1 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.*, 66:1 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I prepared by the improved process of the present invention is selected from the group consisting of:
4-[(3-Bromophenyl)amino]-6-methylaminopyrido-[3,4-d]pyrimidine;

6-(Methylamino)-4-(phenylamino)pyrido[3,4-d]-pyrimidine;
6-(Methylamino)-4-[(3-methylphenyl)amino]pyrido-[3,4-d]pyrimidine;
4-[(3-Chlorophenyl)amino]-6-(methylamino)pyrido-[3,4-d]pyrimidine;
6-(Methylamino)-4-[[3-(trifluoromethyl)phenyl]-amino]pyrido[3,4-d]pyrimidine;
4-[(3-Bromophenyl)amino]-6-[N-(2-hydroxyethyl)methylamino]pyrido[3,4-d]pyrimidine;
4-[(3-Bromophenyl)amino]-6-[(2-hydroxyethyl)amino]pyrido[3,4-d]pyrimidine;
4-[(3-Bromophenyl)amino]-6-[(2,3-dihydroxypropyl)amino]pyrido[3,4-d]pyrimidine; and
4-[(3-Bromophenyl)amino]-6-[N-(2,3-dihydroxypropyl)methylamino]pyrido[3,4-d]pyrimidine; or a pharmaceutically acceptable salt thereof.

A most preferred compound of Formula I prepared by the improved process of the present invention is:
4-[(3-Bromophenyl)amino]-6-methylaminopyrido-[3,4-d]pyrimidine; or a pharmaceutically acceptable salt thereof.

A preferred compound of Formula II prepared according to the second aspect of the present invention is selected from the group consisting of:
4-[(3-Bromophenyl)amino]-6-fluoropyrido[3,4-d]-pyrimidine;
6-Fluoro-4-(phenylamino)pyrido[3,4-d]pyrimidine;
6-Fluoro-4-[(3-methylphenyl)amino]pyrido[3,4-d]-pyrimidine;
6-Fluoro-4-[[(3-trifluoromethyl)phenyl]amino]-pyrido [3,4-d]pyrimidine; and
4-[(3-Chlorophenyl)amino]-6-fluoropyrido[3,4-d]-pyrimidine; or a pharmaceutically acceptable salt thereof.

A preferred novel intermediate of the eighth aspect of the present invention is a compound of Formula II selected from the group consisting of:
6-Fluoro-4-(phenylamino)pyrido[3,4-d]pyrimidine;
6-Fluoro-4-[(3-methylphenyl)amino]pyrido[3,4-d]-pyrimidine;
6-Fluoro-4-[[3-trifluoromethyl)phenyl]amino]-pyrido [3,4-d]pyrimidine; and
4-[(3-Chlorophenyl)amino]-6-fluoropyrido[3,4-d]-pyrimidine; or a pharmaceutically acceptable salt thereof.

As previously described, the compounds of Formula I are useful in inhibiting the epidermal growth factor receptor and related receptors and, in particular, their tyrosine kinase activity and thus are useful in the treatment of proliferative diseases including cancer, psoriasis, proliferative glomerulonephritis and diabetes-induced renal disease, pancreatitis, and as contraceptives.

The process of the present invention in its first aspect is a new, improved, economical, and commercially feasible method for preparing epidermal growth factor inhibitors of Formula I. The process of the present invention in its first aspect is outlined in Scheme I.

Scheme 1

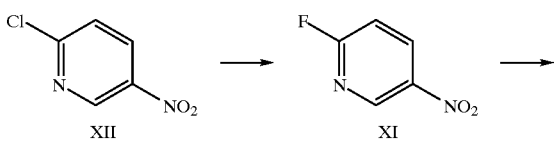

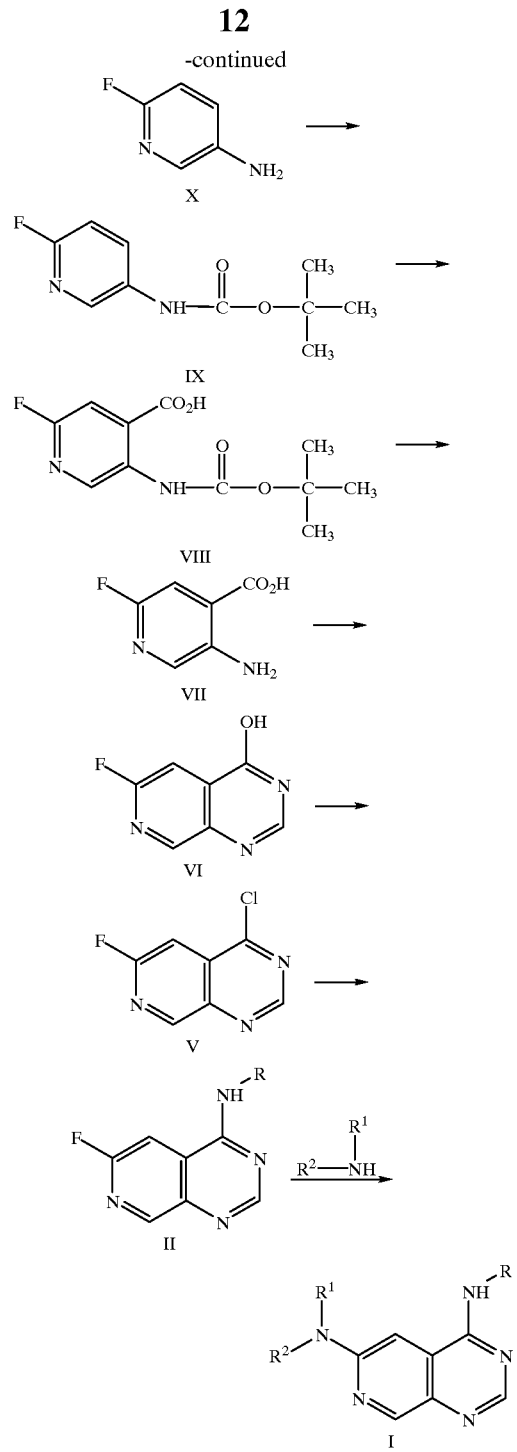

Thus, the compound of Formula XII is treated with a fluoride source such as, for example, a Group I, or Group II metal salt such as, for example, potassium fluoride (KF), cesium fluoride (CsF), calcium fluoride, magnesium fluoride, rubidium fluoride, and the like either alone or combined with a phase transfer catalyst such as, for example, 18-crown-6(1,4,7,10,13,16-hexaoxacyclooctadecane) or tetraphenylphosphonium bromide (see *Tetrahedron Letters,* 28:111–114 (1987)) or organic soluble fluorides such as, for example, tetrabutylammonium fluoride, tetrabutylammonium bifluoride and the like, hydrogen fluoride alone or combined with an amine base such as, for example, triethylamine and the like in a dipolar aprotic solvent such as, for example, N,N-dimethylformamide (DMF), N,N-dimethylacetamide (DMA), 1-methyl-2-pyrrolidinone, dimethyl sulfoxide (DMSO), tetramethylenesulfone (sulfolane) and the like, or a polar aprotic solvent such as, for example, acetonitrile, benzonitrile, acetone, 2-butanone and the like or a nonpolar solvent such as an ether, for example, tetrahydrofuran (THF), 1,4-dioxane, ethylene glycol methyl ether (monoglyme or glyme) (for fluoridation with potassium fluoride sulfolane is preferred whereas for fluoridation with cessium fluoride glyme is preferred) at about 25° C. to about 200° C. to afford the compound of Formula XI (Finger G. C. and Starr, L. O., *J. Am. Chem. Soc.*, 81:2674–2675 (1959)). Preferably, the reaction is carried out with anhydrous cesium fluoride in glyme at about 130° C. or alternatively with anhydrous potassium fluoride in sulfolane at about 120° C. Thus, as exemplified in Example 1, the current process (CsF/glyme) is higher yielding (83%) and proceeds at a much faster rate than the literature procedure (*Tetrahedron Letters*, 28:111–114 (1987)), which utilizes KF/acetonitrile/ tetraphenylphosphonium bromide (60%). Furthermore, the current process does not require any chromatographic purification step, and the product is isolated by simple distillation.

The compound of Formula XI is treated with a reducing agent such as, for example, catalytic hydrogenation over a noble metal catalyst such as, for example, palladium on carbon, platinum oxide, ruthenium and the like, Raney nickel, dissolving metal conditions such as, for example, aluminum on nickel chloride, zinc, tin, iron and the like, hydrazine, stannous chloride, titanium trichloride, sodium dithionite, sulfides, such as, for example, diammonium sulfide and the like, nickel boride, metal hydrides combined with a catalyst such as, for example, sodium borohydride and cobalt chloride and the like in a solvent such as, for example, a lower alkyl alcohol, for example, methanol and the like, a lower alkyl acetate, for example, methyl acetate and the like, an ether, for example, THF and the like, an aromatic hydrocarbon, for example, toluene and the like, a dipolar aprotic solvent, for example, DMF and the like, a lower alkyl carboxylic acid, for example, acetic acid and the like at about 0° C. to about 100° C. to afford the compound of Formula X (Finger G. C., et al., *J. Org. Chem.*, 27:3965–3968 (1962)). Preferably, the reaction is carried out with hydrogen in the presence of 5% palladium on charcoal in toluene at about room temperature or alternatively with hydrogen in the presence of Raney nickel in methanol at about room temperature.

The compound of Formula X is treated with a Boc reagent such as, for example, 2-(tert-butoxycarbonyloxyimino)-2-phenylacetonitrile, tert-butoxycarbonyl azide, di-tert-butyl dicarbonate and the like in a solvent such as, for example, a nonpolar solvent, for example, chloroform, dichloromethane, 1,2-dichloroethane, THF, 1,4-dioxane, chlorobenzene, toluene and the like, a polar aprotic solvent, for example, acetone, acetonitrile, ethyl acetate and the like, a dipolar aprotic solvent, for example, DMF, DMA, 1-methyl-2-pyrrolidinone, DMSO and the like at about −20°C. to about 150° C. to afford the compound of Formula IX. Preferably, the reaction is carried out with di-tert-butyl dicarbonate in 1,4-dioxane at about 8° C. Thus, as exemplified in Example 1, the current process (hydrogenation with Raney nickel followed by Boc protection in 1,4-dioxane) has several advantages over the prior art process. (a) The reduction step can be scaled up when utilizing Raney nickel whereas the scale-up of the 5% Pd/C is problematic. (b) There is a marked solvent effect in the acylation step when utilizing 1,4-dioxane in place of 1,2-dichloroethane. The reaction occurs much faster (3 hours vs 16 hours) and is much cleaner. The net result is that over these two steps, the overall yield for the current process is higher (83% vs 72%), but more importantly, no chromatographic purification is required (product isolated by simple crystallization).

The compound of Formula IX in a solvent such as, for example, a nonpolar hydrocarbon solvent, for example, n-hexane, cyclohexane and the like, an ether, for example, diethyl ether, THF, glyme, 2-methoxyethyl ether and the like (in certain cases coordinating co-solvents such as $N,N,N^1,N^1$-tetramethylethylene-diamine may optionally be used) is treated with a base such as, for example, an alkyl or aryl lithium reagent, for example, tert-butyllithium, sec-butyllithium, butyllithium, phenyllithium either alone or combined with sodium or potassium tert-butoxide, an alkali metal amide, for example, lithium diisopropylamide, sodium diisopropylamide, calcium amide, lithium amide, lithium methylamide, sodium amide, sodium methylamide, potassium amide, potassium methylamide and the like, and a carboxylate source such as, for example, carbon dioxide, a diaryl or dialkyl carbonate, for example, dimethyl carbonate and the like, an alkyl or aryl haloformate, for example, methyl chloroformate, isobutyl chloroformate, and the like (in the case of utilizing carbonate or haloformate reagents, the desired ester can be hydrolyzed to the ester using conventional acid or base hydrolysis), an alkyl or aryl formamide, for example, DMF, N-methylformanilide and the like, followed by oxidation of the derived aldehyde to the carboxylic acid using conventional methodology at a temperature of about −100° C. to about 25° C. to afford the compound of Formula VIII. Preferably, the reaction is carried out in n-butyllithium in the presence of carbon dioxide in diethyl ether and $N,N,N^1N^1$-tetramethylethylenediamine at about −10° C. Thus, as exemplified in Example 1, the major improvement in this step is in the yield. The current process gives the product acid in 47% yield vs 25% of the prior art process. This is due primarily to careful temperature control during the lithiation.

The compound of Formula VIII is treated with a Boc cleaving reagent such as, for example, an organic acid, for example, trifluoroacetic acid, acetic acid and the like, a Lewis acid, for example, aluminum trichloride, boron trichloride, trimethylsilyl triflate and the like, a mineral acid, for example, hydrochloric acid, sulfuric acid, perchloric acid and the like in the presence of a solvent such as, for example, a protic solvent, for example, water and acetic acid for mineral acid reagents, nonpolar solvents, for example, dichloromethane, dichloroethane, chloroform, THF, 1,4-dioxane and the like for organic acids or Lewis acid reagents at about −78° C. to about 100° C. to afford the compound of Formula VII. Preferably, the reaction is carried out with trifluoroacetic acid in dichloromethane at about 25° C. Thus, the current process as exemplified in Example 1 affords the product in 94% yield compared to 74% yield for the prior art process.

The compound of Formula VII is treated with a annulating reagent such as, for example, formamide, formamidine acetate, s-triazine and the like or an amidoacetal such as, for example, DMF dimethyl acetal followed by ammonia catalyzed by alkoxide such as, for example, potassium alkoxide, sodium alkoxide, and the like in a solvent such as, for example, a lower alkyl alcohol, for example, ethanol, propanol, butanol, pentanol and the like, an ether, for example, 4-dioxane, glyme, diglyme and the like, an alkoxy alcohol, for example, 2-methoxyethanol, 2-ethoxyethanol and the like, a dipolar aprotic solvent, for example, formamide and the like at about 50° C. to about 250° C. to afford the compound of Formula VI. Preferably, the reaction is carried out with formamidine acetate in 2-methoxyethanol at reflux temperature. Thus, as exemplified in Example 1, there is a major improvement in yield (77% vs ca 20%) due to the use of formamidine acetate in refluxing 2-methoxyethanol as the ring closure agent as compared to refluxing formamide in the prior art process.

The compound of Formula VI is treated with a chlorinating reagent such as, for example, an inorganic acid chloride, for example, phosphorus trichloride, phosphorus pentachloride, phosphorus oxychloride, thionyl chloride and the like optionally combined with a catalytic amount of DMF; (chloromethylene) dimethylammonium chloride (Vilsmeier reagent), and phosgene iminium chloride in a solvent such as, for example, a nonpolar solvent, for example, chloroform, dichloromethane, 1,2-dichloroethane, THF, 1,4-dioxane, chlorobenzene, toluene and the like at from about 0° C. to about 150° C. to afford the compound of Formula V. Preferably, the reaction is carried out with thionyl chloride in 1,2-dichloroethane at about 85° C.

The compound of Formula V is treated with a compound of Formula IV wherein R is aryl, alkyl, or arylalkyl in a solvent such as, for example a polar protic solvent, for example, a lower alkyl alcohol, for example, methanol, ethanol, 2-propanol and the like, a dipolar aprotic solvent, for example, DMF, 1-methyl-2-pyrrolidinone, DMSO acetonitrile, acetone, and the like optionally in the presence of a catalytic amount of a mineral acid, such as, for example, hydrogen chloride and the like at from about 0° C. to about 150° C. to afford a compound of Formula II wherein R is as defined above. Preferably, the reaction is carried out in 2-propanol at about 80° C. Thus, as exemplified in Example 1, the current process to the chlorofluoro intermediate uses a more convenient chlorinating agent (thionyl chloride) vs the prior art process (phosphorus oxychloride), along with a cosolvent (1,2-dichloroethane) which facilitates scale-up operations. This also makes it convenient to isolate the chlorofluoro intermediate in a fairly pure state to carry on to the next step without the necessity of an aqueous workup. The condensation of this intermediate with the substituted aniline is carried out essentially under the same conditions as the prior art process. The improvements over these two steps increases the yield from 63% to 85.5%.

A compound of Formula II is treated with a compound of Formula III wherein $R^1$ and $R^2$ are the same or different and each is selected from the group consisting of:
hydrogen,
alkyl,
hydroxyalkyl,
aminoalkyl,
diaminoalkyl,
carboxyalkyl,
hydroxyalkylaminoalkyl,
dihydroxyalkylaminoalkyl, and
$R^1$ and $R^2$ may be combined with N to form a 5- or 6-membered ring optionally containing an N, O, or S atom wherein the N atom may be optionally substituted by an alkyl group in a solvent such as, for example, a polar protic solvent, for example, a lower alkyl alcohol and water, for example, methanol, ethanol, 2-propanol and the like; a polar aprotic solvent, for example, acetonitrile, acetone and the like; a dipolar aprotic solvent, for example DMF, 1-methyl-2-pyrrolidinone, DMSO and the like at about 25° C. to about 120° C. to afford a compound of Formula I; and pharmaceutically acceptable salts thereof. Preferably, the reaction is carried out in DMSO at about 80° C. Thus, as exemplified in Example 1, in the current process, there is a major improvement in yield (91%) due to the use of DMSO as solvent as opposed to ethanol in the prior art process (34%). Furthermore, the current process does not require chromatography to purify the target compound.

Compounds of Formula III and Formula IV are either known or capable of being prepared by methods known in the art. Thus, the present process is much higher yielding than the process disclosed in U.S. Pat. No. 5,654,307. The present process provides a compound of Formula I, i.e., Example 1 in 18.2% yield. This is an increase of 53.5-fold over the 0.34% yield in the previous process. Additionally, the present process does not require chromatography and is amenable to large-scale preparations.

The following nonlimiting examples illustrate the inventors' preferred methods for preparing the compounds of the invention.

EXAMPLE 1

4-[(3-Bromophenyl)amino]-6-methylaminopyrido[3,4-d]-pyrimidine

STEP A: Preparation of 2-Fluoro-5-nitropyridine
Method A

A suspension of 160 g (1.01 mol) of 2-chloro-5-nitropyridine and 379 g of dry cesium fluoride was placed in a dry stainless steel bomb which was then charged with 1 L of anhydrous ethylene glycol dimethyl ether. The bomb was sealed, and the reaction was heated at 130° C. with vigorous stirring for 18 hours. The reactor was cooled, vented, and the contents suspended by vigorous agitation. The solids were collected by filtration, then washed well with dichloromethane. The resulting dark brown filtrate was concentrated at 45° C. to give a thick oily brown residue that was distilled through a 4-inch Vigreux column at 61° C./0.05 mm Hg (literature bp 86–87° C./7 mm Hg; Finger G. C. and Starr L. D., *J. Am. Chem. Soc.*, 81:2674–2675 (1959)) to afford 119.4 g (83%) of the product as a clear pale yellow oil, >96% pure by gas chromatography (GC). Nuclear magnetic resonance spectroscopy ($^1$H NMR) in deuterated chloroform (CDCl$_3$): δ9.15 (dd, J=2.7, 0.7 Hz, 1H), 8.63 (td, J=7.7, 2.9 Hz, 1H), and 7.15 (dd, J=9.3, 3.4 Hz, 1H).
Method B A stirred mixture of 25 g (0.158 mol) 2-chloro-5-nitropyridine and 27.5 g (0.474 mol) anhydrous potassium fluoride in 75 mL of sulfolane and 50 mL of benzene was heated to 120° C. as the benzene was allowed to boil off, in order to azeotropically remove any remaining traces of water. The flask was then fitted with an air condenser and a calcium chloride drying tube, and heating was continued for 20 hours. After cooling, the reaction mixture was diluted with 700 mL water, saturated with salt, and steam distilled to give an oily product which was extracted with dichloromethane. Removal of the solvent gave a clear oil which was shown by NMR to contain a small amount of sulfolane. Accordingly, the mixture was chromatographed on 300 g of activity II–III alumina (Merck aluminum oxide 90) eluting initially with hexane, and then with 4:1 hexane:dichloromethane, to give 17.75 g (79%) of the product as an oil.

STEP B: Preparation of 5-Amino-2-fluoropyridine
Method A

A solution of 5 g (35 mmol) 2-fluoro-5-nitropyridine in 100 mL of toluene was hydrogenated over a mixture of 5% palladium on charcoal and anhydrous sodium sulfate until the uptake of hydrogen ceased. The solids were filtered off, the residue was washed with ethyl acetate, and the combined organic solutions were evaporated to give 3.7 (94%) of 5-amino-2-fluoropyridine as a white solid. Recrystallization from dichloromethane-hexanes gave the product mp 89–90° C. (literature mp 87–87.5° C.; Finger G. C., Starr L. D., Roe A., and Link W. J., *J. Org. Chem.*, 27:3965–3968 (1967)). $^1$H NMR (CDCl$_3$): δ7.62 (t, J=2.3 Hz, 1H), 7.11 (td, J=7.7, 3.0 Hz, 1H), 6.72 (dd, J=8.7, 3.3 Hz, 1H), and 3.74 (br s, 2H).

Method B

A stirred solution of 132.4 g (932 mmol) of 2-fluoro-5-nitropyridine in 1.3 L of methanol was hydrogenated at 50.4 pounds per square inch (psi) hydrogen over 40 g of Raney nickel. After 25 hours, the theoretical amount of hydrogen had been taken up. Filtration of the catalyst followed by concentration of tile filtrate afforded 135 g of crude solids that were used directly in the next reaction.

STEP C: Preparation of 5-[N-(tert-Butoxycarbonyl)-amino]-2-fluoropyridine

Method A

A solution of 135 g of crude 5-amino-2-fluoropyridine in 1.3 L of 1,4-dioxane was treated with 225 g (1.03 mol) of di-tert-butyl dicarbonate, and the mixture was heated under nitrogen at 80° C. for 3 hours. The solution was concentrated to a residue that was dissolved in 350 mL of warm tert-butyl methyl ether. The solution was diluted with 350 mL of petroleum ether, then allowed to crystallize in the cold. The solids were collected and dried to give 138 g of product, mp 111–113° C. Concentration and crystallization of the filtrate afforded an additional 27.5 g of product. Total yield=165 g (83% over two steps). A small sample recrystallized from 1:1 methylene chloride:hexanes gave product of mp 113.5–115° C. $^1$H NMR (CDCl$_3$): δ8.07 (br s, 1H), 8.05 (m, 1H), 6.89 (dd, J=9.2, 3.3 Hz, 1H), 6.66 (m, 1H), 1.52 (s, 9H).

Method B

Reaction of a solution of 5.61 g (50 mmol) 5-amino-2-fluoropyridine and 14.2 g (65 mmol) di-tert-butyl dicarbonate in 50 mL of refluxing 1,2-dichloro-ethane for 16 hours followed by workup similar to that described above gave a crude solid that was dissolved in dichloromethane. The solution was chromatographed over 200 g of silica gel eluting first with dichloromethane then with 9:1 dichloromethane:ethyl acetate. The product fractions were recrystallized from 1:1 dichloromethane:hexanes to give 9.32 g (88%) of product, mp 113.5–115° C.

STEP D: Preparation of 5-[N-(tert-Butoxycarbonyl)-amino]-2-fluoropyridine-4-carboxylic acid A mechanically stirred solution of 63.67 g (300 mmol) of 5-[N-(tert-butoxycarbonyl)amino]-2-fluoropyridine, 115 mL of N,N,N',N'-tetramethyl-ethylenediamine, and 1.8 L of dry diethyl ether was cooled to −78° C. in a Nestar refrigeration unit. n-Butyl lithium (72 mL of a 10 molar solution in hexanes) was added dropwise at such a rate so as to maintain the internal reaction temperature below −60° C. The resultant red-colored solution was stored at −40° C. for 16 hours, recooled to −78° C., then charged for ca. 20 minutes with dry carbon dioxide gas introduced via a spurge tube with the rate of bubbling adjusted so as to maintain the internal reaction temperature below −40° C. The reaction flask was removed from the bath and allowed to warm to room temperature over ca. 1 hour. The orange mixture was poured into 700 mL of cold dilute aqueous sodium hydroxide (final pH=12.5). The layers were separated, and the aqueous layer was further extracted with 2×400 mL of diethyl ether. The aqueous layer was ice cooled and acidified to ca. pH 6 with aqueous hydrochloric acid. A sticky precipitate was filtered off, then the filtrate was again ice cooled and further acidified to pH 3.0. A light yellow precipitate was collected by filtration, washed with 200 mL of water, then redissolved in 1 L of 5% aqueous sodium hydroxide. Insoluble matter was removed by filtration and the two-stage acidification/precipitation described above was repeated on the filtrate to provide 36.9 g (47%) of the dried product as a beige solid, mp 253–257° C. (dec). $^1$H NMR in deuterated dimethylsulfoxide [(CD$_3$)$_2$SO]: δ9.83 ppm (s, 1H), 8.85 (s, 1H), 7.49 (d, J$_{H-F}$=2.8 Hz, 1H), 1.48 (s, 9H).

STEP E: Preparation of 5-Amino-2-fluoropyridine-4-carboxylic acid

A suspension of 36.6 g (140 mM) of 5-[N-(tert-butoxycarbonyl) amino]-2-fluoropyridine-4-carboxylic acid hydrated with 0.3 equivalents of water in 280 mL of dichloromethane was cooled in an ice bath then treated dropwise over 15 minutes with 140 mL of trifluoroacetic acid. The bath was removed, and the resultant mixture was stirred at room temperature for 14 hours, then concentrated. The yellow-orange solids were triturated in 125 mL of warm 1:1 diethyl ether:dichloromethane. After cooling, the yellow solids were collected, washed with 100 mL of the diethyl ether:dichloromethane mixture, and dried to afford 19.3 g of product. Processing of the filtrate afforded 1.7 g of a second crop. Total yield=21 g (94%). Recrystallization of a small sample from ethyl acetate provided product of mp 259° C. (dec). $^1$H NMR [(CD$_3$)$_2$SO]: δ8.86 (m, 3H), 7.81 (d, J$_{H-F}$=1.1 Hz, 1H), 7.20 (d, J$_{H-F}$=2.3 Hz, 1H).

STEP F: Preparation of 6-Fluoropyrido[3,4-d]-pyrimidin-4(3H)-one

A suspension of 39.0 g (246 mmol) of 5-amino-2-fluoropyridine-4-carboxylic acid hydrated with 0.15 equivalents of water, 52.01 g (500 mmol) of formamidine acetate, and 500 mL of 2-methoxyethanol was heated at reflux for 6 hours, then concentrated to a solid. The solids were treated carefully with 100 mL of 10% aqueous sodium bicarbonate while maintaining vigorous stirring. The resultant suspension was filtered, and the collected brown solids were washed well with water, then dried over P$_2$O$_5$ to afford 31.3 g (77%,) of product that was used directly in the next reaction. Recrystallization of a small sample from methanol gave product of mp 287° C. (dec).

$^1$H NMR [(CD$_3$)$_2$SO]: δ12.68 (m, 1H), 8.78 (s, 1H), 8.20 (s, 1H), 7.67 (d, J$_{H-F}$=3 Hz, 1H).

STEP G: Preparation of 4-Chloro-6-fluoropyrido-[3,4-d]pyrimidine

A stirred suspension of 30.0 g (182 mmol) of 6-fluoropyrido[3,4-d]pyrimidin-4(3H)-one in 182 mL of 1,2-dichloroethane was treated successively with 182 mL of thionyl chloride, then ca. 1 mL of N,N-dimethyl-formamide. The mixture was heated at reflux for 2.5 hours, then concentrated to a solid that was coevaporated twice with 1,2-dichloroethane. The residual dark brown solids were dissolved in dichloromethane, and the solution was filtered through a short pad of silica gel eluting with dichloromethane. Concentration of product fractions afforded 30.5 g (91%) of pure product after drying. Crystallization of a small sample from tert-butyl methyl ether gave product of mp 75–76° C. $^1$H NMR (CDCl$_3$): δ9.29 (s, 1H, 9.16 (s, 1H), and 7.65 (dd, J=0.7 Hz, 2.0 Hz, 1H).

STEP H: Preparation of 4-[3-Bromophenyl)amino]-6-fluoropyrido [3,4-d]pyrimidine

A mechanically stirred solution of 30.0 g (163 mmol) of 4-chloro-6-fluoropyrido[3,4-d]pyrimidine, 33.75 g (196 mmol) of 3-bromoaniline, and 400 mL of 2-propanol was heated at reflux for 45 minutes. The resulting suspension was concentrated to ca. 150 mL, and the thick yellow precipitate was collected. The filter cake was washed successively with 2% aqueous sodium hydroxide to neutral pH, water, and 2-propanol, then dried over $P_2O_5$ to give 49.1 g (94%) of the product, mp 224–226° C. $^1$H NMR [$(CD_3)_2SO$]: δ10.06 (br s, 1H), 8.94 (s, 1H), 8.73 (s, 1H), 8.23 (br s, 2H), 7.90 (br d, J=7.5 Hz, 1H), 7.39 (t, J=7.8 Hz, 1H), and 7.35 (d, J=8.0 Hz, 1H).

In a process analogous to Step H using appropriate starting materials, the following compounds of Formula II are prepared:

6-Fluoro-4-(phenylamino)pyrido[3,4-d]pyrimidine; mp 224–225.5° C. (crystallization from aqueous methanol)

$^1$H NMR [$(CD_3)_2SO$]: δ10.04 (s, 1H), 8.92 (s, 1H), 8.68 (s, 1H), 8.28 (s, 1H), 7.88 (d, J=7.8 Hz, 2H), 7.44 (t, J=7.8 Hz, 2H), 7.20 (t, J=7.3 Hz, 1H).

6-Fluoro-4-[(3-methylphenyl)amino]pyrido[3,4-d]-pyrimidine; mp 190–192° C. (crystallization from aqueous methanol)

$^1$H NMR [$(CD_3)_2SO$]: δ9.99 (s, 1H), 8.93 (s, 1H), 8.68 (d, $J_{H-F}$=1.8 Hz, 1H), 8.29 (s, 1H), 7.72–7.68 (m, 2H), 7.32 (t, J=8.0 Hz, 1H), 7.02 (d, J=7.4 Hz, 1H), 2.36 (s, 3H).

4-[(3-Chlorophenyl)amino]-6-fluoropyrido[3,4-d]-pyrimidine; mp 224–225° C. (crystallization from aqueous methanol)

$^1$H NMR [$(CD_3)_2SO$]: δ10.11 (s, 1H), 8.97 (s, 1H), 8.76 (s, 1H), 8.28 (s, 1H), 8.14 (t, J=2.0 Hz, 1H), 8.26 (dd, J=8.2, 1.3 Hz, 1H), 7.47 (t, J=8.1 Hz, 1H), 7.24 (dd, J=8.0, 1.4 Hz, 1H).

6-Fluoro-4-[[3-(trifluoromethyl)phenyl]amino]-pyrido [3,4-d]pyrimidine; mp 209–211° C. (crystallization from aqueous methanol)

$^1$H NMR [$(CD_3)_2SO$]: δ10.25 (s, 1H), 8.99 (s, 1H), 8.78 (s, 1H), 8.35 (s, 1H), 8.30 (s, 1H), 8.26 (d, J=8.3 Hz, 1H), 7.68 (t, J=8.0 Hz, 1H), 7.53 (d, J=7.7 Hz, 1H).

STEP I: Preparation of 4-[(3-Bromophenyl)amino]-6-methylaminopyrido [3,4-d]pyrimidine A 2 L stainless steel reactor was flushed with dry nitrogen and charged with 35.0 g (108 mmol) of 4-[3-bromophenyl)amino]-6-fluoropyrido[3,4-d]pyrimidine hydrated with 0.2 equivalents of water, 1 L of dimethyl sulfoxide and 57.5 g (1.85 mol) of anhydrous methylamine. The reactor was sealed and heated at 80° C. for 24 hours, then cooled to room temperature. After venting off the excess methylamine, the contents of the reactor were transferred into a flask with the aid of a small amount of N,N-dimethylformamide. Then the solution was concentrated to ca. 500 mL and poured slowly into 2.5 L of vigorously stirring water. The resultant yellow precipitate was collected, washed well with water, and dried over $P_2O_5$ to afford 34.4 g of crude product. Recrystallization from 400 mL of boiling 2-propanol afforded 30.2 g of product in two crops, mp 181–183° C. The filtrates were further processed by flash silica gel chromatography purification eluting with 0–5% methanol:dichloromethane to provide 2.3 g of additional pure product. Total yield=32.5 g (91%).

$^1$H NMR [$(CD_3)_2SO$]: δ9.71 (br s, 1H), 8.77 (s, 1H), 8.42 (s, 1H), 8.23 (t, J=1.8 Hz, 1H), 7.95 (br d, J=8.4 Hz, 1H), 7.38 (t, J=8.0 Hz, 1H), 7.32 (br d, J=5.0 Hz, 1H), 7.06 (s, 1H), 6.84 (q, J=5.0 Hz, 1H), and 2.90 (d, J=5.0 Hz, 3H).

In a process analogous to Example 1 using appropriate starting materials, the following compounds of Formula I are prepared:

EXAMPLE 2

6-(Methylamino)-4-(phenylamino)pyrido[3,4-d] pyrimidine, mp 212–212.5° C. (crystallization from aqueous methanol)

$^1$H NMR [$(CD_3)_2SO$]: δ9.65 (s, 1H), 8.73 (s, 1H), 8.34 (s, 1H), 7.85 (d, J=7.6 Hz, 2H), 7.41 (t, J=7.6 Hz, 2H), 7.14 (t, J=7.4 Hz, 1H), 7.09 (s, 1H), 6.77 (q, J=5.0 Hz, 1H), 2.89 (d, J=5.0 Hz, 3H).

EXAMPLE 3

6-(Methylamino)-4-[(3-methylphenyl)amino]pyrido [3,4-d]-pyrimidine; mp 189–190° C. (crystallization from aqueous methanol)

$^1$H NMR [$(CD_3)_2SO$]: δ9.57 (s, 1H), 8.72 (s, 1H), 8.34 (s, 1H), 7.69 (br d, J=7.9 Hz, 1H), 7.65 (br s, 1H), 7.29 (t, J=7.8 Hz, 1H), 7.08 (s, 1H), 6.96 (br d, J=7.6 Hz, 1H), 6.76 (q, J=4.9 Hz, 1H), 2.88 (d, J=4.9 Hz, 3H), 2.35 (s, 3H).

EXAMPLE 4

4-[(3-Chlorophenyl)amino]-6-(methylamino)pyrido [3,4-d]-pyrimidine; mp 185.5–187° C. (crystallization from aqueous methanol)

$^1$H NMR [$(CD_3)_2SO$]: δ9.72 (s, 1H), 8.76 (s, 1H), 8.42 (s, 1H), 8.11 (t, J=2.0 Hz, 1H), 7.87 (dd, J=7.9, 2.0 Hz, 1H), 7.43 (t, J=8.1 Hz, 1H), 7.18 (dd, J=7.8, 1.8 Hz, 1H), 7.07 (s, 1H), 6.83 (q, J=4.9 Hz, 1H), 2.89 (d, J=4.8 Hz, 3H).

EXAMPLE 5

6-(Methylamino)-4-[[3-(trifluoromethyl)phenyl] amino]-pyrido [3,4-d]pyrimidine; mp 172–173° C. (crystallization from aqueous methanol)

$^1$H NMR [$(CD_3)_2SO$]: δ9.85 (s, 1H), 8.77 (s, 1H), 8.42 (s, 1H), 8.31 (br s, 1H), 8.27 (br d, J=8.2 Hz, 1H), 7.64 (t, J=8.0 Hz, 1H), 7.47 (br d, J=7.7 Hz, 1H), 7.08 (s, 1H), 6.85 (q, J=4.9 Hz, 1H), 2.90 (d, J=5.0 Hz, 3H).

EXAMPLE 6

4-[(3-Bromophenyl)amino]-6-[N-(2-hydroxyethyl)-methylamino]pyrido[3,4-d]pyrimidine; mp 236–237° C. (Crystallization from methanol)

$^1$H NMR [$(CD_3)_2SO$]: δ9.73 (s, 1H), 8.82 (s, 1H), 8.41 (s, 1H), 8.18 (br s, 1H), 7.93 (br d, J=8.0 Hz, 1H), 7.38 (t, J=8.0 Hz, 1H), 7.33 (br d, J=8.4 Hz, 1H), 7.24 (s, 1H), 4.73 (t, J=5.3 Hz, 1H), 3.76 (t, J=6.1 Hz, 2H), 3.63 (dd, J=6.1, 5.6 Hz, 2H), 3.19 (s, 3).

EXAMPLE 7

4-[(3-Bromophenyl)amino]-6-[(2-hydroxyethyl) amino]pyrido[3,4-d]pyrimidine; mp 209–210° C. (crystallization from methanol)

$^1$H NMR [$(CD_3)_2SO$]: δ9.72 (s, 1H), 8.75 (s, 1H), 8.40 (s, 1H), 8.20 (br s, 1H), 7.91 (br d, J=8.0 Hz, 1H), 7.37 (t, J=8.0 Hz, 1H), 7.31 (br d, J=8.4 Hz, 1H), 7.15 (s, 1H), 6.66 (t, J=5.7 Hz, 1H), 4.80 (t, J=5.3 Hz, 1H), 3.65 (q, J=5.8 Hz, 2H), 3.38 (q, J=6.1 Hz, 2H).

EXAMPLE 8

4-[(3-Bromophenyl)amino]-6-[(2,3-dihydroxypropyl)-amino]pyrido[3,4-d]pyrimidine; mp 186.5–188° C. (crystallization from methanol)

$^1$H NMR [$(CD_3)_2SO$]: δ9.74 (s, 1H), 8.75 (s, 1H), 8.41 (s, 1H), 8.21 (br s, 1H), 7.91 (br d, J=7.9 Hz, 1H), 7.37 (t, J=8.0

Hz, 1H), 7.31 (br d, J=8.4 Hz, 1H), 7.16 (s, 1H), 6.46 (t, J=5.5 Hz, 1H), 4.93 (d, J=4.9 Hz, 1H), 4.68 (t, J=5.5 Hz, 1H), 3.77 (sextet, J=5.5 Hz, 1H), 3.47–3.39 (m, 2H), 3.27-3.20 (m, 2H).

EXAMPLE 9

4-[(3-Bromophenyl)amino]-6-[N-(2,3-dihydroxypropyl)-methylamino]pyrido[3,4-d]pyrimidine; mp 159–160° C. (crystallization from methanol)

$^1$H NMR [(CD$_3$)$_2$SO]: δ9.71 (s, 1H), 8.82 (s, 1H), 8.41 (s, 1H), 8.18 (t, J=1.9 Hz, 1H), 7.93 (br d, J=8.2 Hz, 1H), 7.39 (t, J=8.0 Hz, 1H), 7.33 (br d, J=8.4 Hz, 1H), 7.22 (s, 1H), 4.75 (d, J=4.9 Hz, 1H), 4.59 (t, J=5.7 Hz, 1H), 3.84–3.79 (m, 2H), 3.59 (dd, J=8.7, 6.7 Hz, 1H), 3.41–3.35 (m, 2H), 3.19 (s, 3H).

What is claimed is:

1. A process for the preparation of a compound of Formula I

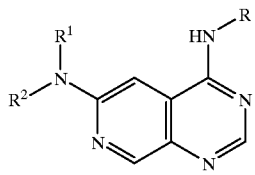

wherein R is aryl, alkyl, or arylalkyl;

R$^1$ and R$^2$ are the same or different and each is selected from the group consisting of:
hydrogen, alkyl, hydroxyalkyl, dihydroxyalkyl, aminoalkyl, diaminoalkyl, carboxyalkyl, hydroxyalkylaminoalkyl, dihydroxyalkylaminoalkyl, and R$^1$ and R$^2$ may be combined with N to form a 5-or 6-membered ring optionally containing an N, O, or S atom wherein the N atom may be optionally substituted by an alkyl group; and pharmaceutically acceptable salts thereof which comprises:

Step (A) reacting a compound of Formula II

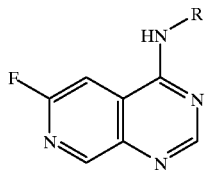

wherein R is as defined above with a compound of Formula III

wherein R$^1$ and R$^2$ are as defined above in a dipolar aprotic solvent to afford a compound of Formula I; and Step (B), if desired, converting a compound of Formula I to a corresponding pharmaceutically acceptable salt by conventional means, and, if so desired, converting the corresponding phramaceutically acceptable salt to a compound of Formula I by conventional means.

2. A process for the preparation of a compound of Formula I

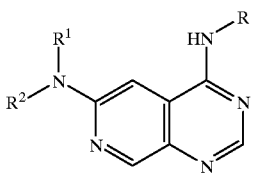

wherein R is aryl, alkyl, or arylalkyl;

R$^1$ and R$^2$ are the same or different and each is selected from the group consisting of:
hydrogen, alkyl, hydroxyalkyl, dihydroxyalkyl, aminoalkyl, diaminoalkyl, carboxyalkyl, hydroxyalkylaminoalkyl, dihydroxyalkylaminoalkyl, and R$^1$ and R$^2$ may be combined with N to form a 5-or 6-membered ring optionally containing an N, O, or S atom wherein the N atom may be optionally substituted by an alkyl group; and pharmaceutically acceptable salts thereof which comprises:

Step (A) reacting the compound of Formula X

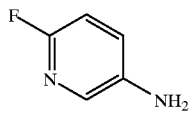

with a Boc reagent in the presence of a nonpolar solvent to afford the compound of Formula IX

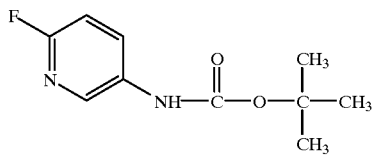

Step (B) reacting the compound of Formula IX with a base at a temperature in the range of –60° C. to –40° C. and a carboxylate source in the presence of a solvent to afford the compound of Formula VIII

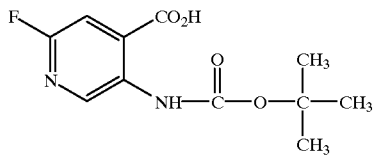

Step (C) reacting the compound of Formula VIII with an organic acid Boc cleaving reagent in a nonpolar solvent to afford the compound of Formula VII

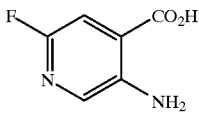

Step (D) reacting the compound of Formula VII with an annulating reagent selected from the group consisting of:

formamide, formamidine acetate,s-triazine;
in a lower alkyl alcohol solvent to afford the compound of Formula VI

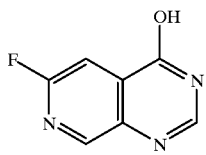

Step (E) reacting the compound of Formula VI with a chlorinating reagent in a nonpolar solvent to afford the compound of Formula V

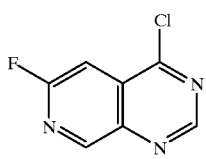

Step (F) reacting the compound of Formula V with a compound of Formula IV

wherein R is defined above in a lower alkyl alcohol solvent to afford a compound of

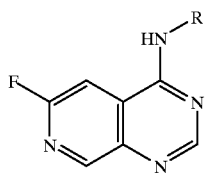

Step (G) reaction of the compound of Formula II with a compound of Formula III

wherein $R^1$ and $R^2$ are as defined above in a dipolar aprotic solvent to afford a compound of Formula I; and Step (H), if desired, converting a compound of Formula I to a corresponding pharmaceutically acceptable salt by conventional means, and, if so desired, converting the corresponding pharmaceutically acceptable salt to a compound of Formula I by conventional means.

3. A process according to claim 2 wherein the Boc reagent in Step (A) is selected from the group consisting of:
2-(tert-butoxycarbonyloxyimino)-2-phenyl-acetonitrile, tert-butoxycarbonyl azide, and di-tert-butyl dicarbonate.

4. A process according to claim 3 wherein the Boc reagent is di-tert-butyl dicarbonate.

5. A process according to claim 2 wherein the base in Step (B) is selected from the group consisting of: phenyllithium, butyllithium, sec-butyllithium, tert-butyllithium, butyllithium and sodium tert-butoxide, tert-butyllithium and potassium tert-butoxide, sec-butyllithium and sodium tert-butoxide, sec-butyllithium and potassium tert-butoxide, butyllithium and sodium tert-butoxide, butyllithium and potassium tert-butoxide, lithium diisopropylamide, sodium diisopropylamide, calcium amide, lithium amide, lithium methylamide, sodium amide, sodium methylamide, potassium amide, and potassium methylamide.

6. A process according to claim 5 wherein the base is selected from the group consisting of: tert-butyllithium, sec-butyllithium, and butyllithium.

7. A process according to claim 2 wherein the carboxylate source in Step (B) is selected from the group consisting of: carbon dioxide, dimethyl carbonate, methyl chloroformate, isobutyl chloroformate, N,N-dimethylformamide, and N-methylformanilide.

8. A process according to claim 7 wherein the carboxylate source is carbon dioxide.

9. A process according to claim 2, wherein the organic acid Boc cleaving reagent in Step (C) is selected from the group consisting of: trifluoroacetic acid, and acetic acid.

10. A process according to claim 9 wherein the Boc cleaving reagent is trifluoroacetic acid.

11. A process according to claim 2, wherein the chlorinating reagent in Step (E) is selected from the group consisting of: phosphorus trichloride, phosphorus pentachloride thionyl chloride, (chloromethylene)dimethylammonium chloride, and phosgene iminium chloride.

12. A process according to claim 11 wherein the chlorinating reagent is thionyl chloride.

13. A process according to claim 2, wherein the nonpolar solvent in Step (E) is selected from the group consisting of: chloroform, dichloromethane, 1,2-dichloroethane, tetrahydrofuran, 1,4-dioxane, chlorobenzene, and toluene.

14. A process according to claim 13, wherein the nonpolar solvent is 1,2-dichloroethane.

15. A process according to claim 2, wherein the lower alkyl alcohol solvent in Step (F) is selected from the group consisting of: methanol, ethanol, and 2-propanol.

16. A process according to claim 15, wherein the lower alkyl alcohol solvent is 2-propanol.

17. A process according to claim 2, wherein the dipolar aprotic solvent is Step (G) is selected from the group consisting of: N,N-dimethylformamide, 1-methyl-2-pyrrolidinone, and dimethyl sulfoxide.

18. A process according to claim 17, wherein the dipolar aprotic solvent is dimethyl sulfoxide.

19. A process according to claim 2 and for the preparation of a compound selected from the group consisting of:
4-[(3-Bromophenyl)amino]-6-methylaminopyrido-[3,4-d]pyrimidine;
6-(Methylamino)-4-(phenylamino)pyrido[3,4-d]-pyrimidine;
6-(Methylamino)-4-[(3-methylphenyl)amino]-pyrido [3,4-d]pyrimidine;
4-[(3-Chlorophenyl)amino]-6-(methylamino)-pyrido [3,4-d] pyrimidine;
6-(Methylamino)-4-[[3-(trifluoromethyl)-phenyl]amino] pyrido[3,4-d]pyrimidine;
4-[(3-Bromophenyl)amino]-6-[N-(2-hydroxyethyl) methylamino]pyrido[3,4-d]pyrimidine;
4-[(3-Bromophenyl)amino]-6-[(2-hydroxyethyl)-amino] pyrido[3,4-d]pyrimidine;
4-[(3-Bromophenyl)amino]-6-[(2,3-dihydroxypropyl) amino]pyrido[3,4-d]pyrimidine; and
4-[(3-Bromophenyl)amino]-6-[N-(2,3-dihydroxy-propyl) methylamino]pyrido[3,4-d]pyrimidine.

20. A process according to claim 19 and for the preparation of 4-[(3-bromophenyl)amino]-6-methylaminopyrido [3,4-d]pyrimidine.

* * * * *